United States Patent [19]

Mandle

[11] Patent Number: 4,673,483

[45] Date of Patent: Jun. 16, 1987

[54] ISOELECTRIC FOCUSING APPARATUS

[75] Inventor: Robert J. Mandle, Lexington, Mass.

[73] Assignee: Ionics Incorporated, Watertown, Mass.

[21] Appl. No.: 842,100

[22] Filed: Mar. 20, 1986

[51] Int. Cl.$^4$ .............................................. B01D 13/02
[52] U.S. Cl. ................................ 204/301; 204/182.3; 204/183.2
[58] Field of Search .................... 204/182.3, 183.2, 301

[56] References Cited

U.S. PATENT DOCUMENTS 4,204,929  5/1980  Bier ...................................... 204/301
4,362,612  12/1982  Bier ...................................... 204/301

Primary Examiner—John F. Niebling
Assistant Examiner—Terryence Chapman
Attorney, Agent, or Firm—Norman E. Saliba

[57] ABSTRACT

The disclosure is directed to an improved apparatus and method for isoelectric focusing whereby the reservoirs and recirculating paths in the apparatus are sealed off from the atmosphere. A liquid is employed which contains buffering compounds capable of maintaining a pH gradient in an electric field. A plurality of permeable diaphragms or membranes are used to separate the flows of liquid while allowing interchange of liquid constituents therebetween. A direct current electrical potential is established transverse to the flow, so as to maintain a gradient of pH steps as between successive channels defined by the membranes, and to separate a mixture of amphoteric substances into said channels.

7 Claims, 3 Drawing Figures

ISOELECTRIC FOCUSING APPARATUS

FIELD OF THE INVENTION

This invention relates to techniques for the separation and/or purification of biological materials and other polymeric amphoteric materials, and more particularly to an improved method and apparatus for isoelectric focusing whereby each reservoir and respective recirculating path in the apparatus is sealed off to the atmosphere thereby preventing any substantial change in the total volume of liquid contained therein.

DESCRIPTION OF PRIOR ART

Isoelectric focusing (IEF) also sometimes called electrofocusing, is an electrophoretic technique for the analysis and micropreparative separation and purification of various biological materials. IEF is based on the fact that certain biomaterials are amphoteric in nature, i.e. are postively charged in acidic media and negatively charged in basic media. At a particular pH value, called the isoelectric point, they have no net charge. In a pH gradient, such materials will migrate under the influence of a D.C. electric field until they reach their isoelectric point where they become immoblized by virtue of their zero electrical mobility. Thus they focus into narrow zones, defined by the pH gradient of the medium and the electric field applied.

IEF techniques employ buffer systems which form stable pH gradients in the electric field. Such buffers are usually composed of synthetic mixtures of many different amphoteric substances having good buffering capacity at their isoelectric points. In the electric field, these components are focused according to their isoelectric points and establish a stable pH gradient. Commercial mixtures of such amphoteric buffer substances are readily available, for example, "Ampholine" and "Pharmolytes". Cuono and Chapo (Electrophoresis, 1982, 3, 65–75) describe a pH gradient for electrofocusing which is generated from a 47-component buffer mixture.

For large scale IEF preparative work, continuous flow instruments are advantageous. Unfortunately, continuous flow electrophoresis in free solutions is plagued by severe boundary distortions caused by several factors: viz., (1) The parabolic nature of liquid flow through confined channels due to viscous drag (flow is fastest through the center of the channel, and decays in a parabolic fashions towards the walls). (2) Electroosmosis at the walls superimposes another type of parabolic flow, this being in a direction perpendicular to the parabolic profile induced by the viscous drag. (3) Density gradients arising from temperature or sample concentration gradients can cause convective flow of liquid.

To overcome these difficulties Martin and Hampson (J. Chrom. 159, 101–110, 1978) reported an appartus for isoelectric focusing with recirculating buffer in channels bounded by membranes. An electric potential was applied perpendicular to the plane of the membranes and a pH gradient was established using simple buffers. Electrode compartments were isolated from the separation cell by means of ion-selective membranes, and Joule heat was dissipated in an external heat exchanger. The membranes used were gels, either supported or unsupported. The major technical problem associated with membrane separators was the electroosmotic flow set up by fixed charges on the membranes or charges on materials such as proteins which absorbed on the membranes. Martin and Hampson prepared amphoteric membranes and reported some success in controlling electoosmotic flow with these membranes.

Bier (U.S. Pat. Nos. 4,204,929 and 4,362,612 which are incorporated herein) developed a similar IEF apparatus with recirculating paths, such that the liquid flowing out of each of 10 streamlined channels is recirculated back to the beginning of the channel with cooling during recirculation. This device used membrane separators with large (1–10 micron) pores. Electroosomotic flow was not addressed in the design of the Bier apparatus. Resolution is restricted by bulk liquid flow through the membrane separators. Bulk liquid flow is caused primarily by electroosmosis. Another source of bulk flow is pressure pulsations set up by the pumping of liquids in the recirculation loop. Both electroosmosis and pumping will decrease the resolving power of the apparatus.

It is the object of the present invention to overcome the stated prior art problems by employing an IEF apparatus and method having an improved capacity for product separation and purification, and which apparatus is simple to operate using a wide range of commercially available membrane separators.

SUMMARY OF THE INVENTION

The following summary and the description of certain of the the figures hereinafter is essentially a repetition of the description found in Bier, U.S. Pat. No. 4,362,612 and is reported herein to avoid referring to an external document in describing the present invention. The present invention however, comprises an improvement over Bier whereby each reservoir and respective recirculating path of the Bier apparatus is sealed off to the atmosphere thereby preventing any substantial change in the total volume of liquid contained in the reservoir, the recirculating path and the respective channel.

The present invention is directed to a method and apparatus for isoelectric focusing on liquids. This flow of liquid to be processed is streamlined by providing a plurality of permeable, generally microporous membranes which define generally parallel channels oriented in a first direction. An electric potential is applied across the streamlined channels of flowing liquid, and isoelectric focusing is achieved on the liquids during the flow thereof since the membranes allow interchange of liquid constituents therebetween while providing the desired streamlining. In a preferred embodiment, a recirculation path is established for each of the streamlined channels by pumping the liquids in each of the recirculation paths, while also providing cooling of the liquids during the recirculation thereof. In this manner, a number of passes are effected to obtain the desired degree of isoelectric focusing. The cooling serves to dissipate the Joule heat generated during IEF in the streamlined channels. Also, in such a preferred embodiment, cooling is accomplished in a return reservoir which can be sealed to thereby close the system to the atmosphere and thus maintain a substantially constant volume in each channel.

In accordance with the apparatus of the invention, there is provided an enclosure having a plurality of inlet ports for receiving the process liquids and a plurality of associated outlet ports opposing the inlet ports. Inlet and outlet separator means are provided for respectively separating the liquids which enter at the inlet ports and exit at the outlet ports. A plurality of permeable membranes are disposed between respective ones of the inlet and outlet separator means and generally parallel to the direction of flow of said liquids. The apparatus also includes means for applying a direct current electrical potential transverse to the direction of flow of said liquids in the enclosure.

In another preferred embodiment of the apparatus of the invention, the streamlining membranes are microporous, having pore sizes in the range of 0.2 to 50 microns, and are more preferably substantially isoporous in which at least 80 percent of the pores have pore sizes within 20 percent of the average pore size. The spacers and membranes are preferably oriented in a vertical position, and process liquids are circulated by means of pumps each operating in conjunction with one of a plurality of recirculation paths for cooling the recirculating process liquids. Means for monitoring the properties of the liquid may also be provided in conjunction with the the recirculation paths. It will be understood that such monitoring means should not allow pressure equalization between the atmosphere and such liquids.

In accordance with the invention, the enclosure is defined by a stack of adjacent, substantially flat, parallel spacers having apertures therein which together form a cavity, and a pair of electrode compartments mounted on opposing ends of the stack, the electrode compartments defining the cavity ends. The spacers have inlet and outlet slots which define the inlet and outlet ports at opposing ends thereof, these ports communicating with the cavity. As stated, inlet and outlet separator means respectively separate the flow of liquids which enter at the inlet ports and exit at the outlet ports. These separator means may comprise, for example, separator spacers which are alternately positioned between the first mentioned spacers, the separator spacers having smaller apertures than the first mentioned spacers, the separator spacers having smaller apertures than the first mentioned spacers and constitute the desired liquid separation means. In this embodiment, the plurality of parallel permeable membranes are mounted in the cavity between the spacers and are operative to streamline the flow of liquids through the cavity. First and second electrode means are respectively mounted in the opposing electrode compartments, and a pair of electrode-confining, substantially hydraulically impermeable membranes separate the cavity from the electrode compartments. The electrode compartments contain electrode buffer solution, and the electrode-confining membranes are of a type which does not allow free passage of liquid while readily allowing passage of electric current.

In accordance with the techniques set forth, applicant obtains advantages over the prior art, including:
1. Provision for an apparatus and process for IEF wherein the liquid volume in each reservoir is maintained substantially constant despite electroosmotic flow or osmotic pressures in the separating channels.
2. Provision for an apparatus and process for IEF wherein the bulk flow of liquid through the separation membranes due to pump oscillations is dampened.

Further features and advantages of the invention will become more readily apparent from the following detailed description when taken in conjunction with the accompanying drawings.

DESCRIPTION OF PREFERRED EMBODIMENTS

Figure 1:
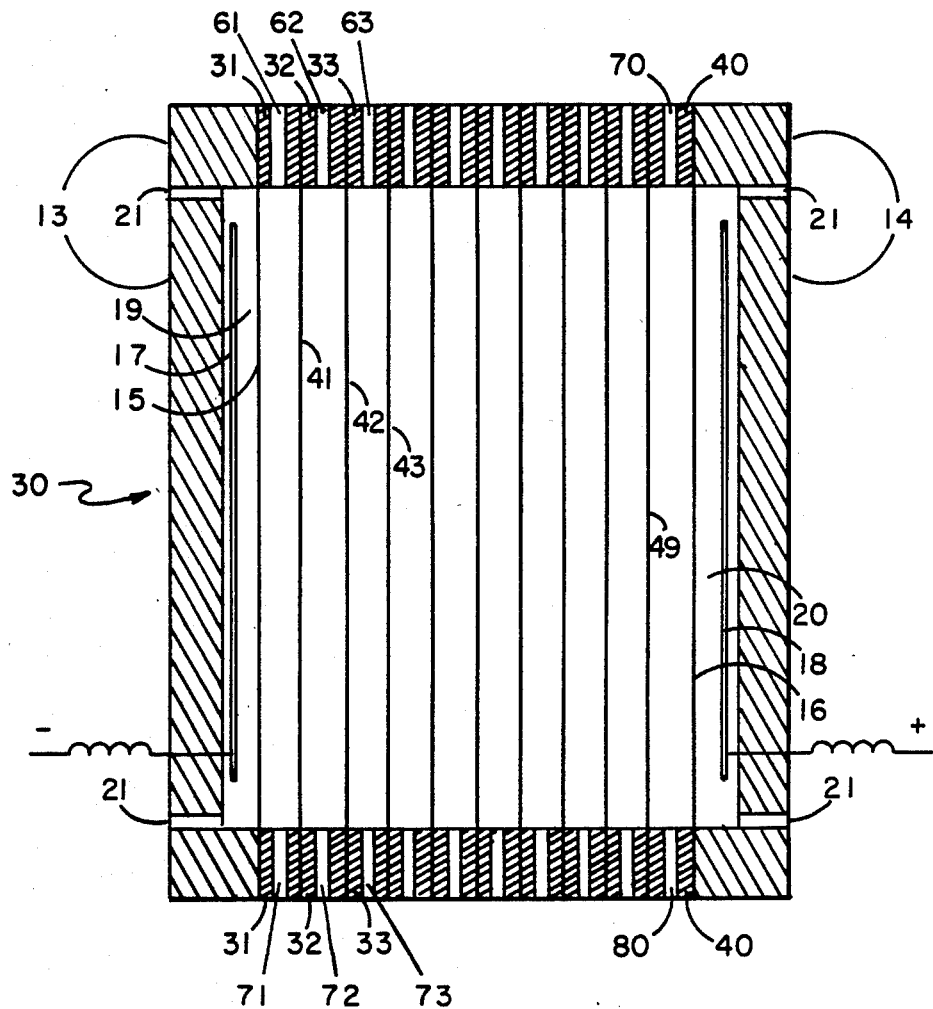
FIG. 1 is a cross-sectional view of an isoelectric focusing apparatus in accordance with an embodiment of the invention.
Figure 2:
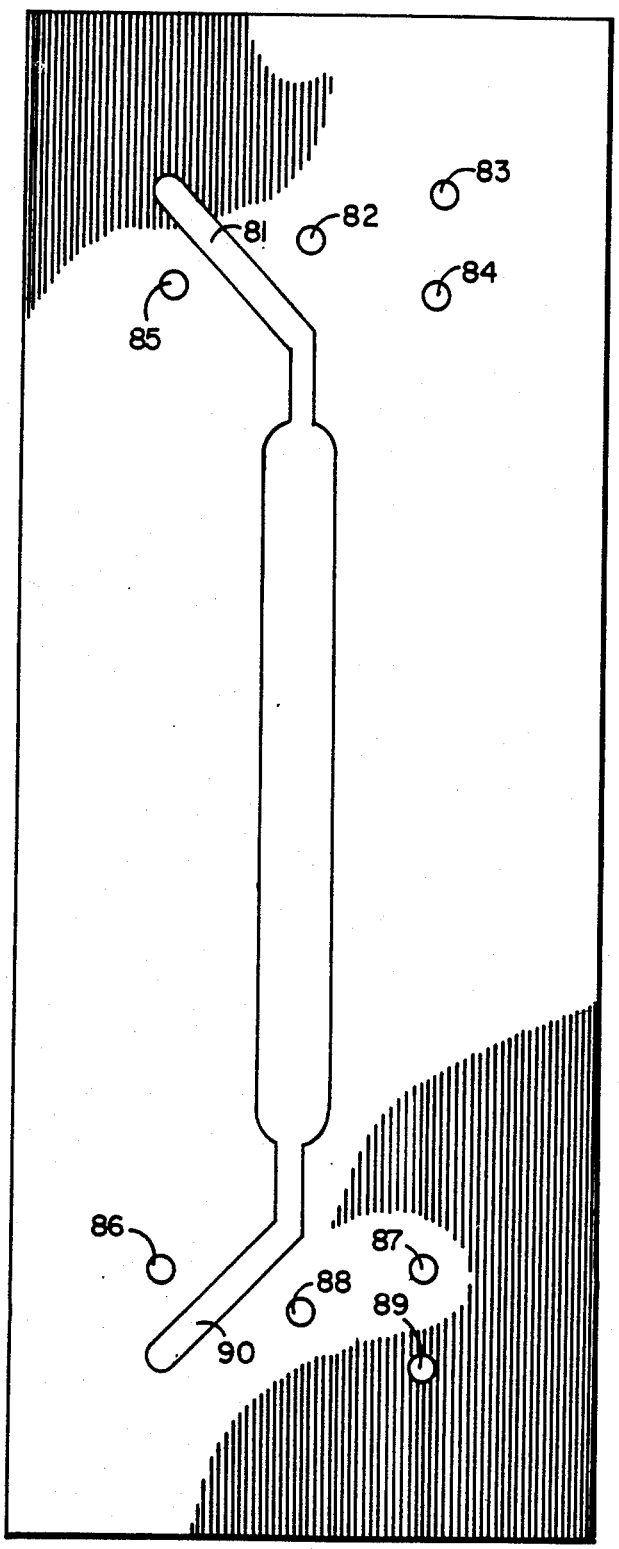
FIG. 2 is a plan view of a channel spacer.

Referring to FIG. 1, there is shown an apparatus having an enclosure 30 defined by a stack of ten substantially flat parallel input/output spacers 31, 32, 33 ... 40. In the present embodiment, the spacers are substantially rectangular in shape and have a central aperture therein, as can be seen in FIG. 2., which illustrates a representative input/output spacer. Between adjacent pairs of input/output spacers are located a permeable membrane. There are, in the FIG. 1 embodiment, nine permeable membranes, designated by reference numbers 41, 42, 43 ... 49. The spacers and membranes are clamped together, by means not shown, between a pair of end plates 13 and 14. The end-plates 13 and 14 have recessed regions 19 and 20 which define the electrode compartments 19 and 20. Ports 21 provide for recycling of electrode buffer solutions and the venting of gaseous products of electrolysis.

The apertures in spacer 31-40 form a cavity and the electrode compartments 19 and 20 on opposing ends of the stack enclose the cavity. The permeable membranes 41, 42, 43 ... 49 divide the cavity of the enclosure 30 into a number of channels. Each input/output spacer 31, 32, 33 ... 40, has a respective inlet port, designated 61, 62, 63 ... 70 and a respective outlet port designated 71, 72, 73 ... 80. The input/output spacer is shown in FIG. 2. with inlet port 81 and outlet port 90, and manifold ducts 82-89. Each manifold duct communicates with only one inlet/outlet port pair and are contiguous through the input/output spacers and through the end-plates 13 and 14 (FIG. 1) which are provided with coextensive ducts and means for tubing attachment. This spacer design permits greater flow of process fluid as duct diameter is not limited by the thickness of the spacer as shown in FIG. 1. Also the distance between the electrodes 17 and 18 can be minimized allowing for greater electrical potential differences across the separation membranes, which increases the speed and resolution of the apparatus. It is understood that various other spacers or structural elements can be employed consistent with the spirit and scope of the invention.

The illustrated number of channels is arbitrary and can be made greater or lesser, depending on the number of fractions desired, although at least five channels are preferred for most applications. The separator membranes 41, 42, 43 ... 49 (FIG. 1) should allow free flow of liquids and passage of the sample material in the liquids. They can be of various types of commercially available filtering membranes or battery separator membranes, as for example, the five micron pore size filter manufactured by Millipore Corp. of Bedford, Mass. For optimal function they should have pore sizes of not less than 0.2 microns, to allow free passage of liquid, and not more than 50 microns to act as effective barriers for flow streamlining. The electrode-confining membranes 15 and 16 should have quite different characteristics, as they should not allow free passage of liquid or sample material but should conduct electric current. Ion selective, substantially hydraulically impermeable membranes, such as manufactured by Ionics, Incorporated, Watertown, Mass. are optimal. The positive electrode 18 should be bounded preferably by a cation selective membrane and the negative electrode 17 by an anion selective membrane. The electrodes can be of platinum, platinized titanium, or other suitable electrode material. The electrode liquids and ampholytes used to establish the pH between channels can be as in conventional IEF and will be familiar to those versed in the art.

Figure 3:
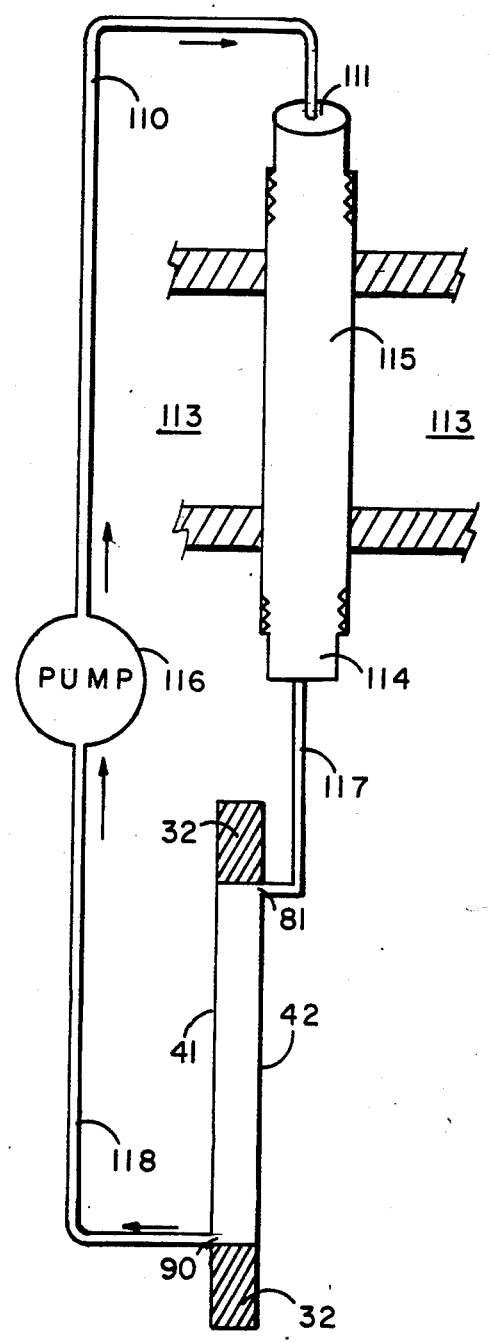
FIG. 3 is an elevated view of a streamlining channel and its associated reservoir.

The improvement of the present invention can be shown by reference to FIG. 3 which diagrams a single sealed recirculation path and its reservoir. The reservoir 115 is surrounded by cooling liquid 113 contained in a heat exchanger (not shown) which serves to control the Joule heating that occurs in the separation cell. Inlet tubing 110 and outlet tubing 117 are connected to the reservoir 115 via end caps 111 and 114 which provide a pressure tight seal so as to isolate the system from the atmosphere. The outlet tubing 117 is connected by tubing attachment means to the endplate 14(FIG. 1) and through coextensive ducts to the input port 81 which is in communication with a separation channel defined by the separation spacer 32 and the membranes 41 and 42 and its output port 90. Return tubing 118 is connected to the output port 90 and by means of a pump 116 liquid is pumped back to the reservoir 115. The advantages of a closed system include: (a) resistance to a volume change in the recirculation loop and its reservoir; (b) the reservoir acts to dampen the pressure pulsations set up by the pump 116 due to the air cushion at the top of each reservoir and (c) the ability to prevent absorbtion of atmospheric gases by the liquid. Such absorbtion may be detrimental to the compounds being focused and thus an inert gas may be used to displace any air in the system.

Any IEF system consistent with a preferred embodiment would include circulation by way of ten closed, (sealed to the atmosphere) loops between the IEF apparatus and the reservoirs located in a heat exchanger connected to a coolant source. A mutichanneled tubing pump would circulate the liquid from the IEF apparatus through sensors which would measure, for example, pH, temperature, ultra violet light absorbance, or other important process parameters. A data recorder and logic system would record data or control the process. A power supply for supplying D.C. power to the appparatus may also be regulated or controlled through the recorder.

EXAMPLE I

In this example there is demonstrated the establishment of a stable pH gradient from pH 2 to pH 11. The recycling mode was used with a ten channel IEF apparatus of the type manufactured by Ionics, Incorporated of Watertown, Mass., wherein the reservoirs were sealed to the atmosphere as in the preferred embodiment. The heat exchanger, with ten reservoirs for sample channels and two for the electrode streams, was maintained at 10 degrees Centigrade. Nitex ® 10 micron separator membranes obtainable from Tetko, Inc. were used between polyethylene separator spacers. Ion selective membranes from Ionics, Incorporated of Watertown, Mass. were used to isolate both electrodes with a cation selective membrane adjacent to the anode and a anion selective membrane adjacent to the cathode. A multichannel peristaltic tubing pump was used to recirculate the liquid at approximately 10 millimeters per minute in each channel. A constant 50 watts of power was supplied from an Isco model 493 power supply, corresponding to a potential of 325 volts per centimeter at equilibrium.

The reservoirs were loaded with a collective 200 milliliters of deionized water containing 5 milliliters of ampholines, (3-10 Pharmacia Chemical Co., Piscataway, N.J.) dilute phosphoric acid (anolyte) and sodium hydroxide (catholyte) were used as electrode solutions. The pH gradient in each channel (1 to 10) was established within 30 minutes and did not substantially change for the next 5.5 hours. The levels in the reservoirs (1 to 10) did not change with time. When the reservoirs were vented to the atmosphere, the cathodic channels, 9 and 10 increased in volume while channels 4, 5, and 6 were depleted of liquid. This disturbance of liquid levels due to electroosmosis was severe enough to require addition of fluid to the reservoirs of channels 5 and 6 and removal of fluid from the cathodic reservoirs.

EXAMPLE II

In this example a low molecular weight peptide, tyrosyltyrosyltyrosine (TYR) was focused in a recycling IEF apparatus similar to Example I except that the separator membranes were of regenerated cellulose having a pore size of 1.2 microns obtained from Satorious Co.

The pH gradient and operating conditions were established as in Example I. When focussing was attempted with open reservoirs, the electroosomotic flow combined with the high hydraulic resistance of the membranes caused the experiment to be terminated. With the open reservoirs, Channels 1 and 2 (adjacent to the anode) drained completely of liquid while Channels 9 and 10 (adjacent to the cathode) overfilled. When the apparatus was operated using the sealed reservoirs of the present invention the results as shown in the Table were obtained with minimal change in liquid levels in the reservoirs. The table shows the liquid level readings with time in Channels 1 to 10.

TABLE

| | Time (Minutes) | | | | | | | | | |
|---|---|---|---|---|---|---|---|---|---|---|
| | 1 | 2 | 3 | 4 | 5 | 6 | 7 | 8 | 9 | 10 |
| 0 | 11.7 | 11.7 | 12.0 | 12.3 | 11.7 | 11.2 | 11.9 | 12.1 | 12.0 | 11.7 |
| 102* | 11.3 | 11.5 | 11.5 | 11.7 | 11.4 | 10.9 | 11.6 | 12.0 | 12.0 | 11.9 |
| 117 | 8.8 | 8.8 | 9.0 | 8.8 | 8.7 | 8.7 | 9.2 | 9.8 | 9.8 | 9.5 |
| 192 | 8.75 | 8.75 | 8.9 | 8.9 | 8.75 | 8.4 | 8.9 | 9.5 | 9.6 | 9.4 |

*The sharp decrease in the liquid level noted after the 102 minutes reading was due to the removal of liquid samples for puposes of analysis.

While there has been described what at present is considered to be the preferred embodiment of the present invention, it will be understood that various modifications and alternatives may be made therein without departing from the scope of the invention and it is intended to cover in the claims appended hereto all such modifications and alternations.

What is claimed is:

1. In an apparatus for isoelectric focusing, comprising, in combination: an enclosure having a plurality of inlet ports and a plurality of associated outlet ports opposing said ports; a plurality of recirculation paths, each coupling an outlet port to a respective inlet port; a liquid within said enclosure and said recirculating paths, said liquid containing buffering components capable of establishing a pH gradient in a direct current electric field; inlet and outlet separator means for respectively separating the flow of liquid which enters at said inlet ports and exist at said outlet ports; a plurality of streamlining membranes disposed between respective ones of said inlet and outlet separator means and oriented generally parallel to the direction of flow of said liquid so as to streamline the flow of liquid as between said inlet and outlet separator means while allowing interchange of liquid constituents therebetween; means for applying a direct current electrical potential transverse the direction of flow of said liquid in said enclosure to establish a gradient of pH steps as between successive channels defined by said membranes; pumping means for pumping the liquid in said recirculation paths for cooling the liquid therein; the improvement comprising a plurality of reservoirs, each connected to a said recirculating path, with each of said reservoir and its respective recirculating path sealed to the atmosphere thereby minimizing any change in the liquid volume of said reservoir, its respective recirculating path and respective channel.

2. Apparatus as defined by claim 1 in which reservoirs are oriented vertically and the flow of liquid is downward such that an air cushion at the top of the reservoir dampens the pulsations of the pumping.

3. Apparatus as defined in claim 1 further comprising means for measuring and recording the properties of the liquid in said recirculation paths.

4. Apparatus as defined by claim 1 wherein said membranes are microporous having pore size in the range of 0.2 to 50 microns.

5. Apparatus as defined in claim 1 in which the membranes are substantially isoporous, each having an average pore size in the range of from about 0.2 to 50 micrometers.

6. Apparatus as defined by claim 1 wherein said spacers and membranes are oriented vertically.

7. Apparatus as defined by claim 1 wherein each recirculation path is adapted to hold at least ten times as much liquid as its respective channel.

* * * * *